United States Patent [19]

Umekawa et al.

[11] Patent Number: 4,647,577

[45] Date of Patent: Mar. 3, 1987

[54] MICROBICIDAL/MICROBISTATIC COMPOSITIONS FOR INDUSTRIAL USE EMPLOYING 4,5-DICHLORO-1,2-DITHIOL-3-ONE AND HALOACETIC ACID ESTERS AS THE ACTIVE AGENTS

[75] Inventors: Osamu Umekawa, Kaizuka; Sakae Katayama, Kobe, both of Japan

[73] Assignees: Katayama Chemical Works Co., Ltd.; Yoshitomi Pharmaceutical Ind., Ltd., both of Osaka, Japan

[21] Appl. No.: 815,174

[22] Filed: Dec. 20, 1985

Related U.S. Application Data

[63] Continuation of Ser. No. 566,208, Dec. 28, 1983, abandoned, which is a continuation of Ser. No. 163,289, Jun. 26, 1980, abandoned.

[30] Foreign Application Priority Data

Jul. 2, 1979 [JP] Japan .................................. 54-84128
Jul. 31, 1979 [JP] Japan .................................. 54-98299

[51] Int. Cl.$^4$ ...................... A01N 37/02; A01N 43/26; A01N 37/06

[52] U.S. Cl. .................................. 514/441; 106/15.05; 162/5; 162/82; 210/755; 252/182; 514/547

[58] Field of Search .................................. 514/441, 547; 106/15.05; 162/5, 82; 210/755; 252/182

[56] References Cited

U.S. PATENT DOCUMENTS

| | | | |
|---|---|---|---|
| 3,839,008 | 10/1974 | Shema et al. | 514/441 |
| 3,879,513 | 4/1975 | Shema et al. | 514/441 |
| 4,022,605 | 5/1977 | Konya et al. | 71/67 |
| 4,289,581 | 9/1981 | Katayama et al. | 514/441 |

FOREIGN PATENT DOCUMENTS

5182723 7/1976 Japan .

Primary Examiner—Allen J. Robinson
Attorney, Agent, or Firm—Stiefel, Gross, Kurland & Pavane

[57] ABSTRACT

This invention relates to microbicidal/microbistatic compositions for industrial use which comprise 4,5-dichloro-1,2-dithiol-3-one and a haloacetic acid ester and an industrial method of killing and/or inhibiting microbes by using the aforementioned compositions.

6 Claims, No Drawings

MICROBICIDAL/MICROBISTATIC COMPOSITIONS FOR INDUSTRIAL USE EMPLOYING 4,5-DICHLORO-1,2-DITHIOL-3-ONE AND HALOACETIC ACID ESTERS AS THE ACTIVE AGENTS

This is a continuation of U.S. application Ser. No. 566,208, filed Dec. 28, 1983, which is a continuation of Ser. No. 163,289, filed June 26, 1980, now both abandoned.

BACKGROUND OF THE INVENTION

1. Field of the Invention

This invention relates to microbicidal/microbistatic compositions for industrial use which comprise 4,5-dichloro-1,2-dithiol-3-one and a haloacetate ester and an industrial method of killing and/or inhibiting microbes by using the aforementioned compositions.

2. Description of the Prior Art

Each of the active ingredients, 4,5-dichloro-1,2-dithiol-3-one and haloacetic acid ester, to be used in accordance with the invention is known. The former compound, 4,5-dichloro-1,2-dithiol-3-one, is known to have strong microbicidal activity, especially against Gram negative bacteria. However, it is difficult to make end-use microbicidal preparations containing this compound for use in industrial waters and papermaking process water because it is sparingly soluble in water. In a known example of its formulation, an aqueous preparation is given which contains a certain surfactant (Japanese Patent Application Kokai No. 82723/1976). However, the above-mentioned compound is susceptible to hydrolysis in aqueous media and, as a result thereof, long-lasting effects cannot be expected.

The other active ingredient, namely a haloacetic acid ester, is generally known to have antimicrobial activity against Gram positive bacteria.

This invention has been completed on the basis of a discovery of component systems in which two types of active ingredients are combined so as to be effective in the majority of media and materials to be treated microbicidally. Moreover, the systems provide synergistic effects as well as long-lasting effects. As a result, it is no longer necessary to identify the microbes and to select an adequate microbicide. Other advantages of the compositions will be made clear from the description hereinbelow.

SUMMARY OF THE INVENTION

This invention relates to novel microbicidal/microbistatic compositions comprising (a) 4,5-dichloro-1,2-dithiol-3-one and (b) a haloacetic acid ester. The compositions of the invention are particularly useful in microbicidal/microbistatic treatment of various industrial media and materials such as water in papermaking processes, industrial, cooling water, heavy oil sludges, cutting oils and textile oils. The compositions of the invention produce a marked effect against a wide variety of microbes present in the aforementioned industrial media and materials. Further, the combined use of the two active ingredients in the composition of the invention produces a synergistically potentiated antimicrobial activity. Due to this synergistic action, the method of treating the various aforementioned industrial media and materials according to the invention provides an advantage in that a very great effect against a wide variety of microbes can be attained with a very small amount of each active ingredient.

DESCRIPTION OF THE PREFERRED EMBODIMENT

Thus, in accordance with the invention, novel liquid microbicidal/microbistatic compositions for industrial use are provided comprising (a) 4,5-dichloro-1,2-dithiol-3-one and (b) a haloacetic acid ester.

According to the invention, the haloacetic acid ester includes compounds represented by the general formula (I)

$$(XCH_2COO-)_n R \qquad (I)$$

wherein $XCH_2COO-$ is directly bound to R, X is a halogen atom, n is an integer of 1 to 3, R is, when n is 1, an alkyl group of up to 18 carbon atoms, which may be substituted by at least one substituent selected from the group consisting of halogen atoms, $-OH$, $-NO_2$, phenyl and $-OR^1$ groups ($R^1$ being a $C_1$ to $C_6$ alkyl or phenyl group optionally substituted by a halogen atom or halogen atoms), when n is 2, a saturated or unsaturated, straight, bivalent hydrocarbon group having 2 to 6 carbon atoms, and when n is 3, a saturated or unsaturated hydrocarbon group having 3 to 6 carbon atoms.

Examples of the compound are: compounds of general formula(I) wherein n is 1, namely monohaloacetic acid esters of the formula $XCH_2COOR$;

n-hexyl monobromoacetate, n-lauryl monobromoacetate, 2-nitro-3-bromo-n-butyl monobromoacetate, benzyl monobromoacetate, 2-n-butoxyethyl chloroacetate, 2-phenoxyethyl bromoacetate, 2-(2-chloroethoxy)ethyl bromoacetate and other substituted alkyl esters;

compounds represented by the formula $XCH_2COOCH_2CH_2OR^2$:

2-n-butoxyethyl monochloroacetate, 2-phenoxyethyl monobromoacetate, 2-(2-chloroethoxy)ethyl monobromoacetate, etc.;

compounds wherein n is 2, namely haloacetic acid diesters of the formula $XCH_2COO-R^3-OCOCH_2X$:

1,2-bis(chloroacetoxy)ethane, 1,2-bis(bromoacetoxy)ethane, 1,2-bis(iodoacetoxy)-ethane, 1,4-bis(chloroacetoxy)-2-butene, 1,4-bis(bromoacetoxy)-2-butene, 1,6-bis(bromoacetoxy)-3-hexyne, bis(chloroacetoxy)ethane and bis(bromoacetoxy)ethane; and compounds wherein n is 3, namely haloacetic acid triesters:

1,2,3-tris(bromoacetoxy)propane.

Table 1 summarizes preferred haloacetate esters with their boiling points, specific gravities and refractive indexes as well as solubilities therein of 4,5-dichloro-1,2-dithiol-3-one.

TABLE 1

| Compound | Chemical name | Boiling point °C./mm Hg | Specific gravity $d_4^{20}$ | Refractive index $n_D^{25}$ | Solubility (28° C.) |
| --- | --- | --- | --- | --- | --- |
| No. 1 | n-hexyl monobromoacetate | 124/25 | 1.2465 | 1.4542 | >22% |

TABLE 1-continued

| Compound | Chemical name | Boiling point °C./mm Hg | Specific gravity $d_4^{20}$ | Refractive index $n_D^{25}$ | Solubility (28° C.) |
|---|---|---|---|---|---|
| No. 2 | n-lauryl monobromoacetate | 151–153/3 | 1.0480 | 1.4605 | >22% |
| No. 3 | 2-nitro-3-bromo-n-butyl monobromoacetate | 130/0.3 | 1.7876 | 1.5060 | 32% |
| No. 4 | benzyl monobromoacetate | 145/4 | 1.432 | — | 32% |
| No. 5 | 2-n-butoxyethyl monochloroacetate | 120–123/5 | 1.3530 | 1.4378 | >22% |
| No. 6 | 2-n-butoxyethyl monobromoacetate | 123–124/3 | 1.6450 | 1.4570 | >22% |
| No. 7 | 2-phenoxyethyl monochloroacetate | 156/2 | 1.5233 | 1.5377 | 41% |
| No. 8 | 2-phenoxyethyl monobromoacetate | 172/3 | 1.8079 | 1.5378 | 35% |
| No. 9 | 2-phenoxyethyl monoiodoacetate | 175/3 | 2.0306 | 1.5643 | 32% |
| No. 10 | 2-(2-chloroethoxy)-ethyl monobromoacetate | 123–124/2 | 1.9320 | 1.4840 | 40% |
| No. 11 | 1,2-bis(chloroacetoxy)-ethane | 122–125/2 | 1.408 | 1.4694 | >22% |
| No. 12 | 1,2-bis(bromoacetoxy)-ethane | 144–145/2 | 1.833 | 1.5077 | >22% |
| No. 13 | 1,2 bis(iodoacetoxy)-ethane | — | 2.223 | 1.5725 | >22% |
| No. 14 | 1,4-bis(chloroacetoxy)-2-butene | — | 1.346 | 1.4860 | >22% |
| No. 15 | 1,4-bis(bromoacetoxy)-2-butene | 197–198/0.5 | 1.761 | 1.5233 | >22% |
| No. 16 | 1,2,3-tris(bromoacetoxy) propane | 230–235/2 | 1.9886 | 1.5270 | >22% |

The solubility values (%) given in Table 1 were calculated by using the following formula:

$$\frac{\text{Weight of 4,5-dichloro-1,2-dithiol-3-one}}{\text{Weight of 4,5-dichloro-1,2-dithiol-3-one plus haloacetate ester}} \times 100\%$$

The expression ">22%" means that the solute was homogeneously soluble up to a concentration of 22% but any dissolution test had not been made at higher possible concentrations.

Generally, the compositions of the invention contain both the ingredients in such a proportion that (a) 4,5-dichloro-1,2-dithiol-3-one amounts to 0.1 to 90% by weight and the (b) haloacetic acid ester correspondingly amounts to 99.9 to 10% by weight. In accordance with one aspect of this invention (a) 4,5-dichloro-1,2-dithiol-3-one amounts to 0.1 to 45% by weight and the (b) haloacetic acid ester correspondingly amounts to 99.9 to 55% by weight. In accordance with another aspect of this invention (a) 4,5-dichloro-1,2-dithiol-3-one amounts to 10 to 90% by weight, (preferably 15 to 85%) and the (b) haloacetic acid ester correspondingly amounts to 90 to 10% by weight (preferably 85 to 15%). In accordance with a further aspect of this invention 4,5-dichloro-1,2-dithiol-3-one amounts to 0.1 to 25% by weight and the (b) haloacetic acid ester correspondingly amounts to 99.9 to 75% by weight. In accordance with another aspect of the invention, ingredient (a) amounts to 0.1 to 10% by weight and ingredient (b) amounts to 99.9 to 90% by weight.

The compositions of the invention need not contain any organic solvent or surfactant besides the above two components. If desired, however, they may contain an organic solvent and/or surfactant.

Preferably, both active ingredients are generally used in accordance with the invention as a preparation containing both ingredients at adequate concentrations or two preparations each containing its own active ingredient at an adequate concentration. Such a preparation may be made by dissolving the active ingredients in an appropriate organic solvent to make a solution and, if necessary, further adding a surfactant. Since the active ingredient (a) is only slightly soluble in water, as mentioned above, non-aqueous preparations are most preferred. When the proportion of the active ingredient (a) is small, it is also possible to make preparations with the active ingredient (a) and active ingredient (b) alone. Of course, the invention covers the cases where the active ingredients (a) and (b) are used separately, each as its own preparation. Further, the haloacetate ester can be added per se without making it into a preparation, as the case may be. Furthermore, sometimes the use of a solvent is unfavorable to the media or materials to be treated, and in such case, the active ingredients alone may be added.

Examples of the solvent adequate to make the above-mentioned preparations are dimethylformamide, diethylformamide, methyl cellosolve, ethyl cellosolve, phenyl cellosolve, diethylene glycol monomethyl ether, propylene glycol monomethyl ether, dipropylene glycol monomethyl ether, tripropylene glycol monomethyl ether, isopropyl alcohol, diethylene glycol, dipropylene glycol, polypropylene glycol, acetone and methyl isobutyl ketone. Suitable surfactants are, for example, such nonionic ones as alkylolamides, N,N,N',N'-polyoxypropylene-polyoxyethyleneethylenediamines or nonylphenyl reaction product with 9–12 molecules of ethylene oxide.

As previously mentioned, the compositions of the present invention are used for microbicidal/microbistatic purposes. The systems to be treated microbicidally/microbistatically with the compositions of this invention include any media or materials used for industrial use or manufactured or produced commercially and required to be treated microbicidally/microbistatically, such as process water in papermaking, industrial cooling water, washing water, heavy oil sludges, cutting oils, lignin-containing waste liquors, water paints, antifouling paints, latexes, textile oils and other liquid targets. Further, the compositions of this invention can be used as preservatives and/or antifungal agents, e.g., for starch, fibrous wall materials, and other solids.

The two ingredients (a) and (b) may be added simultaneously or at different times with some time interval to the media or materials to be treated microbicidally. In the case of addition at different times, it is preferable to first add ingredient (a) and then ingredient (b) some time later. By doing so, the number of viable microbes is first decreased sharply by the action of ingredient (a) and then the growth of microbes is inhibited for a long period of time by the action of ingredient (b).

The level of addition of the compositions of this invention depends upon the target materials to be subjected to microbicidal/microbistatic treatment, such as those mentioned above. Generally, however, levels of addition of about 0.05 to 1000 ppm will be adequate for microbicidal/microbistatic purposes, however, levels of 1 to 1000 ppm are preferable. Thus, for example, in the case of addition to process water in the papermaking process, they are used generally at concentrations within the range of 0.05 to 100 ppm, preferably 1 to 100 ppm, more preferably, 1 to 50 ppm and most preferably, 5 to 50 ppm, to attain microbicidal/microbistatic effects, although the concentrations depend upon the state of adhesion of slime, the kinds of slime-forming bacteria and so forth. Further, to overcome the troubles caused by sludge in heavy oil, levels of addition of 5 to 50 ppm are employed, and, when the compositions are used as preservatives or antifungal agents for cutting oils, they are used at concentrations of 5 to 1000 ppm.

The compositions of the invention act in a very ideal manner in view of the mechanism of action. Thus, when the compositions are added to systems to be treated, 4,5-dichloro-1,2-dithiol-3-one, owing to its excellent microbicidal activity, will cause at once a rapid decrease in the number of viable microbes and subsequently the haloacetic acid ester will inhibit the growth of microbes (microbistatic activity) in a continuous manner. If 4,5-dichloro-1,2-dithiol-3-one is added alone, it will exhibit at first a remarkable effect to decrease the number of viable microbes but will be exhausted due to hydrolysis thereof with the lapse of time, so that the number of viable microbes will increase again to the original one. On the other hand, in cases where the haloacetic acid ester is added alone, relatively higher concentrations and a fairly long period of exposure are required, especially when the number of microbes is large.

The compositions of the invention have a broad antimicrobial spectrum. For example, they are markedly active against Gram negative bacteria such as those belonging to the genera Pseudomonas, Escherichia, Flavobacterium and Achromobacter, as well as Gram positive bacteria such as those belonging to the genera Bacillus, Staphylococcus and Micrococcus. They are not only active against bacteria but also active against and can control such fungi belonging to Aspergillus, Trichoderma, Geotrichum, Penicillium and Fusarium. As a result, they can control most of the problem microbes and consequently can be used as prompt measures against troubles caused by microbes in systems where various bacteria and fungi are present, without any need of such prior investigation of the kinds of microbes and concentrations thereof followed by selection of agents adequate to the respective cases as has hitherto been required. Moreover, as previously stated, it is only necessary to add active ingredients (a) and (b) to obtain the desired result.

When viewed as preparations or formulations, the compositions can be said to add to the practicality of the active ingredient 4,5-dichloro-1,2-dithiol-3-one, which is rather unstable and not so soluble, by formulating it up to a considerable concentration of about 40% so as to provide liquid preparations which are stable and favorable in use. The reason for the stability of the compositions of the invention is that the haloacetic acid esters as solvents are acidic compounds and 4,5-dichloro-1,2-dithiol-3-one is stable in such acidic media. In addition to the above-mentioned storage stability, the liquid preparations of the invention, when added to various systems, remain intact and act effectively without causing precipitation of crystals.

Since the haloacetic acid esters, which act as active ingredients and at the same time as solvents, have each a high specific gravity, the compositions of the invention are liquids each of a high specific gravity. Therefore, when they are used in papermaking processes, they will not float on the process water surface and never cause such problems as oil spots resulting from their being caught by paper. Further, being hardly miscible with water, the preparations, when added to water systems, settle on the bottom of the equipments or vessels in the water systems and are gradually dissolved into the water systems, so that it is not necessary to add them constantly even in such systems as papermaking systems where water flows constantly. Thus, the number of additions can be reduced. Impact feeding can also achieve the intended effects to a satisfactory extent.

Further, the compositions of the invention do not cause foaming in the systems to which they are added and are not corrosive to the machines or equipments. In addition, when they are added in papermaking processes, they do not cause any decrease in quality of paper or any problems in papermaking. Still further, the combined use of the two ingredients, (a) 4,5-dichloro-1,2-dithiol-3-one and (b) the haloacetic acid ester, produces a synergistically potentiated antimicrobial activity. The synergism is especially evident when the ratio of (a):(b) is 8:2, 2:8, 4:6 and 6:4, for instance. Owing to the synergistic action, the method of the invention provides an advantage in that a very great effect against a wide variety of microbes can be attained with a very small amount of each ingredient.

The following tests and examples illustrate the invention in more detail.

TEST 1

Bactericidal Effect Against *Pseudomonas aeruginosa*

A bouillon medium was inoculated with *Pseudomonas aeruginosa* and incubated at 37 C. for 20 hours. The culture solution was diluted 100-fold with sterilized water and 10 ml portions of the dilution were poured into sterilized test tubes. Thereto were added mixtures of (a) 4,5-dichloro-1,2-dithiol-3-one and (b) bis(bromoacetoxy)ethane in various proportions in an active ingredient concentration of 1 ppm. (Each of (a) and (b) was dissolved in dimethylformamide (DMF) and the two solutions were mixed to prepare the mixtures. Care was taken that the volume of the mixture did not exceed 0.1 ml). After shaking for an hour to cause sufficient contact between the ingredients and microbes, the number of surviving microbes was determined by the plate dilution method.

Separately but simultaneously, the number of surviving microbes was determined by the same procedure for the case where the microbes were exposed to the same amounts of 4,5-dichloro-1,2-dithiol-3-one as those in the various mixtures added in the above tests. The respective test results are shown in Table 2 and Table 3.

When no active ingredients were added, the number of viable bacteria was $3.7 \times 10^7$/ml.

TABLE 2

| Ratio (a):(b) | Number of viable bacteria per ml |
|---|---|
| 10:0 | $1.2 \times 10^6$ |
| 8:2 | $1.0 \times 10^3$ |
| 6:4 | $1.6 \times 10^7$ |
| 4:6 | $1.9 \times 10^7$ |
| 2:8 | $2.3 \times 10^7$ |
| 0:10 | $2.5 \times 10^7$ |

TABLE 3

| Level of addition of (a) (ppm) | Number of viable bacteria per ml |
|---|---|
| 1 | $1.2 \times 10^6$ |
| 0.8 | $8.1 \times 10^6$ |
| 0.6 | $1.7 \times 10^7$ |
| 0.4 | $2.4 \times 10^7$ |
| 0.2 | $2.1 \times 10^7$ |

When the ratio of 4,5-dichloro-1,2-dithiol-3-one to bis(bromoacetoxy)ethane was 8:2, a marked decrease in the number of bacteria was observed and thus a synergistic effect against *Pseudomona aeruginosa* was proved.

TEST 2

Bactericidal effect against *Bacillus subtilis*

Using *Bacillus subtilis* and using bis(bromoacetoxy)ethane and 1,4-bis(bromoacetoxy)-2-butene each as a haloacetic acid ester, the bactericidal effect was examined by the same procedure as in Test 1, except that the total concentration of the ingredients added was 0.1 ppm. When no ingredients were added, the number of viable bacteria was $2.3 \times 10^6$/ml. The results are shown in Table 4 and Table 5.

TABLE 4

| Ratio (a):(b) | Number of viable bacterial per ml | |
|---|---|---|
| | (b) = bis(bromoacetoxy)ethane | (b) = 1,4-bis(bromoacetoxy)-2-butene |
| 10:0 | $1.9 \times 10^4$ | $1.9 \times 10^4$ |
| 8:2 | $5.9 \times 10^3$ | $1.2 \times 10^3$ |
| 6:4 | $4.4 \times 10^5$ | $1.9 \times 10^5$ |
| 4:6 | $1.9 \times 10^6$ | $2.1 \times 10^6$ |
| 2:8 | $2.1 \times 10^6$ | $2.1 \times 10^6$ |
| 0:10 | $2.0 \times 10^6$ | $2.1 \times 10^6$ |

TABLE 5

| Level of addition of (a) (ppm) | Number of viable bacteria per ml |
|---|---|
| 0.1 | $1.9 \times 10^4$ |
| 0.08 | $6.8 \times 10^4$ |
| 0.06 | $1.3 \times 10^5$ |
| 0.04 | $1.5 \times 10^6$ |
| 0.02 | $1.9 \times 10^6$ |

When the ratio of 4,5-dichloro-1,2-dithiol-3-one to either of the two haloacetate esters was 8:2, a marked decrease in the number of bacteria and thus a synergistic effect was ascertained.

TEST 3

Effect in white water

In a certain paper mill, white water was sampled from the second ply site of a cylinder 5-ply linerboard machine. The white water had a pH of 6.8 and contained viable microbes mainly consisting of Micrococcus, Flavobacterium and Pseudomonas species. The (10) ml portions of the white water were poured into sterilized test tubes, and thereto were added mixtures of (a) 4,5-dichloro-1,2-dithiol-3-one and (b) bis(bromoacetoxy)ethane in various proportions in a concentration of 0.5 ppm. (Each of (a) and (b) was dissolved in DMF and the two solutions were mixed to prepare the mixtures. Care was taken that the volume of the mixture did not exceed 0.1 ml.) After shaking for an hour to cause sufficient exposure to the ingredients, the number of surviving microbes was determined by the plate dilution method. The results are shown in Table 6. When no ingredients were added, the number of viable bacteria was $4.0 \times 10^6$/ml.

TABLE 6

| Ratio (a):(b) | Number of viable bacteria per ml |
|---|---|
| 10:0 | $4.8 \times 10^3$ |
| 8:2 | $6.2 \times 10^2$ |
| 6:4 | $4.5 \times 10^4$ |
| 4:6 | $2.4 \times 10^5$ |
| 2:8 | $3.0 \times 10^5$ |
| 0:10 | $> 10^6$ |

TEST 4

Effect in white water

In a certain paper mill, white water was sampled at the second ply (cylinder) site of a linerboard machine (Fourdrinier-cylinder combination machine). The white water had a pH of 6.4 and contained viable microbes mainly consisting of Flavobacterium, Micrococcus and Bacillus species. The same test as in Test 3 was performed with this white water. The results are shown in Table 7. When no ingredients were added, the number of viable microbes was $2.6 \times 10^5$/ml.

TABLE 7

| Ratio (a):(b) | Number of viable bacteria per ml |
|---|---|
| 10:0 | $2.8 \times 10^4$ |
| 8:2 | $1.9 \times 10^4$ |
| 6:4 | $1.7 \times 10^4$ |
| 4:6 | $7.5 \times 10^3$ |
| 2:8 | $1.8 \times 10^4$ |
| 0:10 | $2.6 \times 10^5$ |

When the ratio (a):(b) was 4:6, a marked decrease in the number of bacteria was observed and thus a synergistic effect could be verified.

TEST 5

Antimicrobial test with a standard organism

Aliquots of a bouillon medium were poured into L-shaped test tubes and thereto were added (a) 4,5-dichloro-1,2-dithiol-3-one and (b) bis(bromoacetoxy)ethane each in the form a solution in DMF so that various concentrations resulted in the medium.

A preculture of *Bacillus subtilis* (standard strain) was added in a certain specified quantity to each L-shaped test tube and shake culture was performed at an optimum growth temperature.

The growth of the microbe was measured at appropriate time intervals by using a photoelectric colorimeter (570 mμ) for preparing a growth curve. The complete inhibition concentration, namely the concentration at which the curve, at the time point when the control culture with no active agents added reached a steady state, did not show any rise of the logarithmic stage, was determined. The results of this test are shown in Table 8.

TABLE 8

| Agent added* | Complete inhibition concentration (ppm) |
|---|---|
| (a) alone | 0.8 |
| (b) = bis(bromoacetoxy)-ethane alone | 10.0 |
| (a):(b) = 2:8 | 1.0 |
| (a):(b) = 4:6 | 1.3 |

*(a) alone - 0.08 ml of a DMF solution of (a) having a concentration of 100 ppm was added.
(b) alone - 0.1 ml of a DMF solution of (b) having a concentration of 1000 ppm was added.
(a):(b) = 2:8 - 0.1 ml of a DMF solution containing (a) and (b) in a ratio of (a):(b) = 2:8 and having a total concentration of (a) plus (b) of 100 ppm was added.
(a):(b) = 4:6 - 0.1 ml of a DMF solution containing (a) and (b) in a ratio of (a):(b) = 4:6 and having a total concentration of 100 ppm was added.

COMPARATIVE TEST

Microbicidal concentrations of each agent used alone

A bouillon medium was inoculated with each respective standard strain microbe and incubated at an optimum growth temperature. The culture solution was diluted 100 times with sterilized water and 10-ml portions of the dilution were poured into sterilized test tubes. The active ingredient was added in various concentrations. The mixtures were shaker at the optimum growth temperature for an hour for causing sufficient contact between the agent and the microbe, and then the number of surviving microbes was determined by the plate dilution method. The active agents added were in the form of DMF solutions and in quantities given below.

| Microbicidal concentration (ppm) | Concentration in DMF solution (ppm) | Quantity added (ml) |
|---|---|---|
| 0.1 | 100 | 0.01 |
| 0.15 | 100 | 0.015 |
| 0.3 | 100 | 0.03 |
| 2 | 1000 | 0.02 |
| 10 | 1000 | 0.1 |
| 100 | 10000 | 0.1 |
| 200 | 100000 | 0.02 |
| 300 | 100000 | 0.03 |

The results of this microbicidal activity test are shown in Table 10.

In Table 10 and also Table 11 and 12 the meaning of the numbers in the tables is set forth in the description of Test 8, especially in the second paragraph of Test 8.

TABLE 10

| | bacillus subtilis | Pseudomonas aeruginosa | Flavobacterium aquatile | Micrococcus lysodeikticus |
|---|---|---|---|---|
| | | (ppm) | | |
| 4,5-Dichloro-1,2-dithiol-3-one | 0.1 | 0.3-2 | 2 | 0.15 |
| Bis(chloroacetoxy)-ethane | >10 | >200 | — | — |
| 1,4-Bis(chloroacetoxy)-2-butene | >10 | >200 | — | — |
| Bis(bromoacetoxy)-ethane | >10 | >200 | >300 | 100 |
| 1,4-Bis(bromoacetoxy)-2-butene | >10 | >200 | — | — |
| Bis(iodoacetoxy)-ethane | >10 | >200 | — | — |

TEST 6

Synergistic effect

A synergistic effect test was performed in the same manner as in the above comparative test and the results as shown in Table 11 and Table 12 were obtained.

TABLE 11

Effect against *Bacillus subtilis*

| Haloacetate ester | (a):(b) | Microbicidal concentration (ppm) |
|---|---|---|
| 1,4-Bis(chloroacetoxy)-2-butene | 4:6 | 0.1 |
| 1,4-Bis(bromoacetoxy)-2-butene | 8:2 | 0.1 |

TABLE 12

Effect Against *Pseudomonas Aeruginosa*

| Haloacetate ester | (a):(b) | Microbicidal concentration (ppm) |
|---|---|---|
| Bis(bromoacetoxy)ethane | 4:6 | 2 |
| Bis(iodoacetoxy)ethane | 8:2 | 2 |
| 1,4-Bis(bromoacetoxy)-2-butene | 4:6 | 2 |

TEST 7

A preparation was made by dissolving 4,5-dichloro-1,2-dithiol-3-one at a concentration of 10% in 1,4-bis(-bromoacetoxy)-2-butene.

A bouillon medium was inoculated with *Pseudomonas aeruginosa* and incubated at 37° C. for 20 hours. The culture solution was diluted 100-fold with sterilized water and 10 ml portions of the dilution were poured into sterilized test tubes. The above preparation was added in a specified concentration to aliquots of the suspension, which were then shaken at 37° C. At each specified time point, each medium was sampled and the number of viable bacteria was determined. Separately, each of the both ingredients contained in the preparation was used along and its effect was judged by the same procedure. The results are shown in Table 13.

TABLE 13

| | Agent | | |
|---|---|---|---|
| | Combination preparation | 4,5-Dichloro-1,2-dithiol-3-one | 1,4-Bis(bromoacetoxy)-2-butene |
| | | Concentration | |
| Contact period | 5 ppm | 0.5 ppm | 4.5 ppm |
| Before contact | $9.5 \times 10^8$ | $9.5 \times 10^8$ | $9.5 \times 10^8$ |
| 0.5 hour | $1.6 \times 10^5$ | $5.2 \times 10^5$ | $9.5 \times 10^8$ |
| 1 hour | $3.7 \times 10^4$ | $3.3 \times 10^4$ | $9.5 \times 10^8$ |
| 2 hours | $1.7 \times 10^3$ | $4.6 \times 10^3$ | $9.0 \times 10^8$ |
| 4 hours | $<10^3$ | $<10^3$ | $8.5 \times 10^8$ |
| 8 hours | $<10^3$ | $<10^3$ | $7.6 \times 10^8$ |
| 16 hours | $<10^3$ | $2.4 \times 10^4$ | $5.1 \times 10^8$ |
| 24 hours | $<10^3$ | $1.5 \times 10^8$ | $4.3 \times 10^8$ |
| 36 hours | $2.4 \times 10^3$ | $3.9 \times 10^8$ | $4.0 \times 10^8$ |
| 48 hours | $5.3 \times 10^4$ | $8.4 \times 10^8$ | $3.2 \times 10^8$ |

(Each numerical value indicates the number of viable bacteria per ml.)

Although 4,5-dichloro-1,2-dithiol-3-one is high in bactericidal activity at early stages, its efficacy in single use thereof lasts only for 8 hours after the addition. On the other hand, single use of 1,4-bis(bromoacetoxy)2-butene does not change the number of viable bacteria in a significant manner although a slight tendency toward decrease is observable. As compared with these, the combination preparation which contains both the ingredients at first causes an immediate and sharp decrease in the number of viable bacteria and thereafter remains effective for a long period of time.

TEST 8

Effects of Various Combination Preparations against Bacteria

Combination preparations were made by dissolving 4,5-dichloro-1,2-dithiol-3-one in a concentration of 5% in various haloacetic acid esters.

Test culture solutions were prepared by suspending bacteria of each specified species in a concentration of the order of $10^6$/ml and each preparation was added in various concentrations. The culture solutions were shaken at 37 C. for an hour and then the number of viable bacteria was determined. The concentration at which the number of viable bacteria was of the order of $10^3$/ml or less is termed "effective concentration".

In Table 14, there are shown effective concentrations for the above combination preparations. In the table, Compounds Nos. 1-16 correspond to the respective compounds shown in Table 1.

TABLE 14

| | Microorganism | | |
|---|---|---|---|
| Compound No. | Pseudomonas aeruginosa | Bacillus subtilis | Escherichia coli |
| 1 | 5 ppm | 3 ppm | 6 ppm |
| 2 | 6 | 4 | 6 |
| 3 | 5 | 4 | 6 |
| 4 | 5 | 3 | 5 |
| 5 | 6 | 4 | 6 |
| 6 | 6 | 4 | 6 |
| 8 | 6 | 4 | 6 |
| 9 | 5 | 3 | 4 |
| 10 | 6 | 3 | 5 |
| 11 | 6 | 4 | 6 |
| 12 | 5 | 3 | 5 |
| 13 | 4 | 2 | 4 |
| 14 | 6 | 4 | 6 |
| 15 | 5 | 3 | 5 |
| 16 | 6 | 4 | 6 |
| 4,5-Dichloro-1,2-dithiol-3-one | 0.3 | 0.2 | 0.3 |

TEST 9

Liquid preparations were made by dissolving 4,5-dichloro-1,2-dithiol-3-one at a concentration of 5% in 1,2-bis(bromoacetoxy)ethane and 1,4-bis(bromoacetoxy)-2-butene, respectively and stored in a thermostat at 40° C. or 20° C. for a month, and the possible change in physical properties and in antimicrobial activity after the lapse of time was studied.

After a month of storage, the preparations did not present any change in appearance. No precipitation of crystals was found. Gas chromatographic analysis failed to reveal any change of chemical nature.

The effective concentrations for both the preparations as required to decrease the number of viable bacteria from $10^6$/ml to $10^3$/ml or less were determined by the procedure of Test 8 using Pseudomonas aeruginosa as test organism. They were as shown in Table 15.

TABLE 15

| | | Bactericidal activity (Effective concentration) | |
|---|---|---|---|
| Haloacetate ester in the preparation | Storage condition | Immediately after preparation | After a month of storage |
| 1,2-Bis(bromoacetoxy)ethane | 20° C. | 5 ppm | 5 ppm |
| | 40° C. | 5 | 5 |
| 1,4-Bis(bromoacetoxy)-2-butene | 20° C. | 5 | 5 |
| | 40° C. | 5 | 5 |

COMPARATIVE EXAMPLE

Degradation of a haloacetate ester in alcoholic preparations

Diethylene glycol and methyl Cellosolve (ethylene glycol monomethyl ether) were respectively added in a concentration of 20% to 1,2-bis(bromoacetoxy)ethane purified by vacuum distillation. The resulting solutions were stored in a thermostat at 37° C. for a month. The solutions before and after the storage were each injected into a gas chromatograph. The chromatograms obtained with the solutions before the storage each showed two main peaks of the solvent and 1,2-bis(bromoacetoxy)ethane together with some peaks of impurities contained in either of the constituents. However, after the storage, the peak of the solvent had almost disappeared and a new peak was found. This is presumed to be due to a reaction of the solvent with 1,2-bis(bromoacetoxy)ethane.

EXAMPLE 1

In a certain petrochemical plant, an on-site test was conducted using a combination of 4,5-dichloro-1,2-dithiol-3-one and lauryl bromoacetate in an open-type circulation cooling tower holding 600 m³ of water. Slime mainly composed of Zoogloea species was found adhering to the sprinkler plate and the cold water pit walls of the cooling tower, and $5.8 \times 10^6$/ml of viable bacteria were detected in the circulating cooling water. In the test, 4,5-dichloro-1,2-dithiol-3-one was added at once to the warm water pit and 60 minutes later, lauryl bromoacetate was added at once to the warm water pit. The number of viable microbes in the cold water pit was determined at intervals. The level of addition of 4,5-dichloro-1,2-dithiol-3-one was 5 ppm based on the amount of water retained in the cooling system and that of lauryl bromoacetate was 50 ppm on the same basis. Each agent was added in the form of a 10% solution in dimethylformamide. The results of the viable bacteria counting were as shown in the following table. A prolonged period of the test use resulted in disappearance of the slime within the system and improvement in heat exchanger performance.

| Water tested | Number of viable microbes per ml |
| --- | --- |
| Before addition of the first agent | $5.8 \times 10^6$ |
| 30 minutes after addition of the first agent | $6.5 \times 10^4$ |
| 50 minutes after addition of the first agent | $4.0 \times 10^4$ |
| 30 minutes after addition of the second agent | $2.7 \times 10^3$ |
| 60 minutes after addition of the second agent | $7.5 \times 10^3$ |
| 90 minutes after addition of the second agent | $9.0 \times 10^3$ |
| 120 minutes after addition of the second agent | $4.2 \times 10^4$ |
| 240 minutes after addition of the second agent | $4.8 \times 10^6$ |

EXAMPLE 2

Antifungal test with a stamp material

Problems were encountered due to contamination of a stamp material* with mold fungi belonging to Paecilomyces.

*which contained molasses and was to be used as a binder in constructing furnace linings.

Therefore, a preparation (Preparation A) consisting of 20 parts by weight of 4,5-dichloro-1,2-dithiol-3-one, 5 parts by weight of n-hexyl bromoacetate and 75 parts by weight of methyl Carbitol (diethylene glycol monomethyl ether) was added to the stamp material at a dose of 500 ppm based thereon. Similarly, but separately, a preparation (Preparation B) consisting of 20 parts of 4,5-dichloro-1,2-dithiol-3-one and 80 parts of methyl Carbitol was added at a dose of 500 ppm. Each stamp material sample (100 g) was poured into a dish and kept at a constant temperature of 27° C. and observed for change with the lapse of time. The antifungal efficacy was evaluated in accordance with the following criteria:

—: No fungal growth.

+: Colonies covered not more than one third of the sample surface.

++: Colonies covered more than one third of the sample surface.

| Sample | After (days) | | | | | | | |
| --- | --- | --- | --- | --- | --- | --- | --- | --- |
| | 1 | 3 | 5 | 10 | 20 | 30 | 40 | 60 |
| Control (no active agent added) | — | + | + | ++ | ++ | ++ | ++ | ++ |
| Preparation A added | — | — | — | — | — | — | — | + |
| Preparation B added | — | — | — | — | + | + | ++ | ++ |

EXAMPLE 3

In a certain raw coat paper mill, the number of viable bacteria in the saveall white water was found to be $4.8 \times 10^6$/ml. The number of viable bacteria in the paper stock in the waste stuff chest where waste stuff (or broke) was disintegrated for reuse was $8.7 \times 10^7$/ml. This mill had thitherto added slime control agents containing methylenebisthiocyanate or bromine-containing compounds as main active ingredients. However, there had been frequent slime-caused problems rendering a 2-week continuous operation impossible. Therefore, 4,5-dichloro-1,2-dithiol-3-one was added to the waste stuff chest at an addition level of 5 ppm based on the waste stuff volume in the impact feeding mode three times a day, while 1,2-bis(bromoacetoxy)ethane was added once a day for 8 hours to the saveall in an amount such that its concentration in water amounted to 5 ppm. Slime formation was prevented throughout the 2-week continuous operation carried out in this manner, and thus good results were obtained. The number of viable microbes in white water, when the two agents were combined, decreased remarkably, as shown in the following table.

| | Number of viable microbes per ml in | |
| --- | --- | --- |
| | Paper stock in waste stuff chest to which 4,5-dichloro-1,2-dithiol-3-one was added | Saveall white water to which 1,2-bis (bromoacetoxy)-ethane was added |
| Before addition | $8.7 \times 10^7$ | $4.8 \times 10^5$ |
| After 1 hour of addition | — | $5.0 \times 10^4$ |
| After 3 hours of addition | — | $3.0 \times 10^4$ |
| After 5 hours of addition | — | $2.8 \times 10^4$ |
| After 7 hours of addition | — | $2.5 \times 10^4$ |
| 30 minutes after discontinuance of addition | $4.3 \times 10^3$ | $8.0 \times 10^4$ |
| 60 minutes after discontinuance of addition | $2.5 \times 10^3$ | $4.5 \times 10^5$ |

EXAMPLE 4

In a certain wood free paper mill, 4,5-dichloro-1,2-dithiol-3-one was added to the white water pit of a papermaking machine in a continuous manner for 6 hours a day so that a concentration in water of 2 ppm was obtained. In two weeks of continuous operation in this manner, multilayered bacterial slime was found adhering to the walls of the saveall of the machine. Then, the machine was washed, and 1,4-bis(bromoacetoxy)-2-butene was added in a continuous manner for 8 hours a day such that a concentration in water of 10 ppm was obtained, and the operation was continued in this manner. In a week, pink slime mainly composed of Flavobacterium species was found on the walls of the saveall and stock inlet and the continuous operation was no more possible. Therefore, the machine was washed, and 4,5-dichloro-1,2-dithiol-3-one and 1,4-bis(bromoacetoxy)-2-butene were added together for 6 hours a day such that concentrations in water of 1 ppm and 4 ppm, respectively, were obtained. Slime formation was scarcely observed even after 4 weeks of continuous operation, and thus the productivity was greatly improved.

ments at intervals for gas generation and number of viable microbes. The results are shown in the following table.

| Sample | After lapse of | | | | |
|---|---|---|---|---|---|
| | 1 days | 5 days | 10 days | 30 days | 60 days |
| Waste liquor without the preparation added | | | | | |
| Viable microbes per ml | $5.0 \times 10^4$ | $8.2 \times 10^6$ | $2.7 \times 10^7$ | $3.0 \times 10^7$ | $3.5 \times 10^2$ |
| Gas generation | 1 ml | 10 ml | 20 ml | 25 ml | 25 ml |
| Waste liquor with the preparation added | | | | | |
| Viable microbes per ml | $5.2 \times 10^2$ | $< \times 10^2$ | $< \times 10^2$ | $< \times 10^2$ | $< \times 10^2$ |
| Gas generation | 0 ml | 0 ml | 0 ml | 0 ml | 0 ml |

EXAMPLE 5

Inhibition of sludge formation in heavy oil

Oil solutions having the compositions given below were respectively added in concentrations specified below to portions of a heavy oil (commercially available one), and the heavy oil samples were inoculated with a kerosene dilution of sludge sampled in a ship and allowed to stand at 37° C. for 3 weeks, for examination of sludge formation. The results are shown in the table given below.

| Composition | Composition A | Composition B | Composition C |
|---|---|---|---|
| 4,5-Dichloro-1,2-dithiol-3-one | 8 | 10 | — |
| 2-Phenoxyethyl monochloroacetate | 12 | — | 20 |
| Xylene | 38 | 38 | 38 |
| Kerosene | 40 | 40 | 40 |
| Polyoxyethylene nonylphenol ether | 2 | 2 | 2 |

(in parts by weight)

| | Results |
|---|---|
| Concentration | Sludge formation |
| Blank | Severe |
| Composition A | |
| 10 ppm | No formation |
| 20 ppm | No formation |
| Composition B | |
| 10 ppm | Severe |
| 20 ppm | Slight |
| Composition C | |
| 10 ppm | Severe |
| 20 ppm | Severe |

EXAMPLE 6

Antifungal test with waste liquor in pulp manufacture

In a certain kraft pulp plant, foaming and/or decomposition/degeneration took place in a storage tank for a lignin-containing waster liquor produced from the pulp manufacturing process. Examination of microbes in the waste liquor revealed that Saccharomyces yeast fungi were causing fermentation. A preparation composed of 4,5-dichloro-1,2-dithiol-3-one and 2-nitro-3-bromo-n-butyl bromoacetate in a ratio of 2:8 was added at an addition level of 50 ppm. The liquor did not foam any longer, but could be stored for 2 months without any appreciable decomposition. 30 ml each of the waste liquors before and after addition of the preparation was placed in an Einhorn tube and subjected to measure-

EXAMPLE 7

In a certain paper mill, pink slime formed in a paper machine for coat paper raw stock (production: 120 tons/day). A preparation made by dissolving 4,5-dichloro-1,2-dithiol-3-one in a concentration of 1% in 1,2-bis(bromoacetoxy)ethane was added to the machine chest twice a day, each time for two hours, at an addition level of 20 ppm based on the sum of stock and clear water inflows. As a result, the pink slime disappeared, and troubles, such as spot formation, were completely prevented.

EXAMPLE 8

In a certain paper mill, the number of viable bacteria in white water in a wood free paper machine (production: 60 tons/day) was $10^6$/ml and a large quantity of slime was found. After washing the paper machine with water under high pressure, a preparation made by dissolving 4,5-dichloro-1,2-dithiol-3-one in a concentration of 5% in 1,2-bis(bromoacetoxy)ethane was added to the stuff box once a day for 8 hours at a level of 10 ppm based on the stock and clear water inflows. As a result, the number of viable bacteria decreased to $10^3$/ml or less, and the incidence of slime formation also decreased to a remarkable extent.

EXAMPLE 9

In a certain paper mill, the number of viable bacteria in white water in 6-ply linerboard machine (production: 30 tons/day) was $10^7$/ml and a large quantity of slime was found. A preparation made by dissolving 4,5-dichloro-1,2-dithiol-3-one in a concentration of 0.5% in 1,4-bis(bromoacetoxy)-2-butene was added to each machine chest for each ply two times a day, each time for 2 hours, at a level of 50 ppm based on the stock inflow. As a result, the number of viable bacteria decreased to $10^3$ to $10^4$/ml, the amount of slime gradually decreased and the incidence of troubles such as paper break decreased sharply.

EXAMPLE 10

In a certain chemical plant, in a cooling tower system retaining 500 tons of water in a soybean oil purification process, a large quantity of slime formed within the tower due to contamination of cooling water with nutrients such as soybean oil. A preparation made by dissolving 4,5-dichloro-1,2-dithiol-3-one in a concentration of 20% in 1,4-bis(bromoacetoxy)-2-butene was added once every other day at an addition level of 15 ppm based on the water retained by the system. As a results, slime peeled off and the cooling efficiency was improved.

EXAMPLE 11

In a certain petrochemical plant, tests were carried out by adding the following two kinds of preparations to a cooling tower system retaining 400 tons of water (rate of circulation: 2,000 tons/hour).

Preparation 1:
4,5-Dichloro-1,2-dithiol-3-one: 10.0 weight %
Ethylene oxide-propylene oxide block copolymer derivative of ethylenediamine: 0.5 weight %
Phenyl Cellosolve: 50.0 weight %
Polyethylene glycol: 39.5 weight %

Preparation 2:
4,5-Dichloro-1,2-dithiol-3-one: 10.0 weight %
1,2-Bis(bromoacetoxy)ethane: 90.0 weight %

Preparation 1 was added at a site near the intake of the cold water pit at a level of 50 ppm based on the water retained in the system. The number of viable bacteria in the circulating water was measured before the addition and several times at intervals after the addition.

One week after the addition of Preparation 1, Preparation 2 was tested in the same manner. The results are shown in Table 16.

TABLE 16

| Number of bacteria at the time point | Test preparation | |
|---|---|---|
| | Preparation 1 | Preparation 2 |
| Before addition | $3.3 \times 10^6$ | $3.0 \times 10^6$ |
| 1 hour after addition | $6.2 \times 10^4$ | $8.3 \times 10^4$ |
| 2 hours after addition | $4.3 \times 10^3$ | $1.2 \times 10^3$ |
| 4 hours after addition | $<10^3$ | $<10^3$ |
| 8 hours after addition | $<10^3$ | $<10^3$ |
| 16 hours after addition | $1.2 \times 10^3$ | $<10^3$ |
| 24 hours after addition | $3.0 \times 10^5$ | $4.0 \times 10^3$ |
| 36 hours after addition | $1.8 \times 10^6$ | $9.5 \times 10^3$ |
| 48 hours after addition | $2.8 \times 10^6$ | $5.0 \times 10^4$ |

What is claimed is:

1. A composition having biocidal and biostatic activity against microorganisms selected from the group consisting of Gram positive bacteria, Gram negative bacteria, and fungi, said composition comprising (a) 0.5 to 25 percent by weight 4,5-dichloro-1,2-dithiol-3-one and (b) 99.5 to 75 percent by weight of a haloacetic acid ester selected from the group consisting of 1,4-bis(bromoacetoxy)-2-butene and 1,2-bis(bromoacetoxy)-ethane.

2. The composition of claim 1 wherein the amount of the 4,5-dichloro-1,2-dithiol-3-one is 0.5 to 10 percent by weight and the amount of the haloacetic acid ester is 99.5 to 90 percent by weight.

3. A method of killing or inhibiting the growth of microorganisms in a medium, the microorganisms being selected from the group consisting of Gram negative bacteria, Gram positive bacteria, and fungi, said method comprising adding to the medium 4,5-dichloro-1,2-dithiol-3-one and a haloacetic acid ester selected from the group consisting of 1,4-bis(bromoacetoxy)-2-butene and 1,2-bis(bromoacetoxy)-ethane wherein the percent by weight ratio of the 4,5-dichloro-1,2-dithiol-3-one to the haloacetic acid ester is from 0.5–40:99.5–60 and the total concentration of the 4,5-dichloro-1,2-dithiol-3-one and the haloacetic acid ester in the medium is from about 0.05 to about 1,000 ppm.

4. The method of claim 3 wherein the percent by weight ratio of the 4,5-dichloro-1,2-dithiol-3-one to haloacetic acid ester is from 0.5–25:99.5–75.

5. The method of claim 3 wherein the 4,5-dichloro-1,2-dithiol-3-one and the haloacetic acid ester are added simultaneously to the medium.

6. The method of claim 3 wherein the 4,5-dichloro-1,2-dithiol-3-one is added to the medium prior to the addition of the haloacetic acid ester.

* * * * *